United States Patent
Resl

(10) Patent No.: US 10,446,046 B2
(45) Date of Patent: Oct. 15, 2019

(54) METHOD FOR MODIFYING A DRIVING SIMULATOR

(71) Applicant: AVL LIST GMBH, Graz (AT)

(72) Inventor: Michael Resl, Graz (AT)

(73) Assignee: AVL LIST GMBH, Graz (AT)

(*) Notice: Subject to any disclaimer, the term of this patent is extended or adjusted under 35 U.S.C. 154(b) by 234 days.

(21) Appl. No.: 15/030,723

(22) PCT Filed: Oct. 9, 2014

(86) PCT No.: PCT/EP2014/071633
§ 371 (c)(1),
(2) Date: Apr. 20, 2016

(87) PCT Pub. No.: WO2015/071033
PCT Pub. Date: May 21, 2015

(65) Prior Publication Data
US 2016/0260343 A1    Sep. 8, 2016

(30) Foreign Application Priority Data
Nov. 13, 2013 (AT) .............................. A 50755/2013

(51) Int. Cl.
*G09B 9/052* (2006.01)
*A61B 5/18* (2006.01)
(Continued)

(52) U.S. Cl.
CPC .......... *G09B 9/052* (2013.01); *A61B 5/02405* (2013.01); *A61B 5/0531* (2013.01);
(Continued)

(58) Field of Classification Search
CPC ... G09B 9/052; A61B 5/02405; A61B 5/0531; A61B 5/18; A61B 5/4884; A61B 5/024;
(Continued)

(56) References Cited

U.S. PATENT DOCUMENTS

| | | | |
|---|---|---|---|
| 5,075,881 A | 12/1991 | Blomberg et al. | |
| 5,694,939 A | 12/1997 | Cowings | |
| 2003/0149344 A1* | 8/2003 | Nizan | A61B 5/486 600/300 |

FOREIGN PATENT DOCUMENTS

| | | |
|---|---|---|
| DE | 10152852 | 5/2003 |
| DE | 102006016716 | 10/2007 |

(Continued)

OTHER PUBLICATIONS

Machine Translation of DE 10 2006 016716 A1 to Bensch, et al.*
(Continued)

*Primary Examiner* — Robert P Bullington
(74) *Attorney, Agent, or Firm* — Whitmyer IP Group LLC

(57) ABSTRACT

A method for modifying a driving simulator is disclosed. During at least one time segment of an actual drive, a chronological profile of a biometric state of the athlete is determined, a chronological profile of a parameter of a vehicle used by the athlete is determined, and a relationship is determined between the chronological profile of the biometric state and parameter of the vehicle. During a first training in the driving simulator a developing chronological training profile of the biometric state of the athlete is determined, and during a further, second training in the driving simulator, the chronological training profile of the biometric state of the athlete, modified by mental stimulation of the athlete according to the determined relationship, is made to approximate the chronological profile of the biometric state of the athlete in the actual drive.

15 Claims, 3 Drawing Sheets

(51) Int. Cl.
    *A61B 5/024*     (2006.01)
    *A61B 5/053*     (2006.01)
    *A61B 5/00*     (2006.01)
    *A61M 21/00*     (2006.01)

(52) U.S. Cl.
    CPC .............. *A61B 5/18* (2013.01); *A61B 5/4884* (2013.01); *A61B 5/024* (2013.01); *A61B 5/0533* (2013.01); *A61M 2021/0005* (2013.01)

(58) Field of Classification Search
    CPC ......... A61B 5/0533; A61M 2021/0005; B60K 28/06
    USPC .......................................................... 434/65
    See application file for complete search history.

(56) References Cited

FOREIGN PATENT DOCUMENTS

| | | | | |
|---|---|---|---|---|
| DE | 102006016716 A1 | * | 10/2007 | ............. G09B 9/052 |
| JP | 2011140262 A | | 7/2011 | |
| KR | 20090033193 | | 4/2009 | |
| WO | 9007365 | | 7/1990 | |

OTHER PUBLICATIONS

English Abstract of DE102006016716.
English Abstract of DE10152852.
English Abstract of KR20090033193.

* cited by examiner

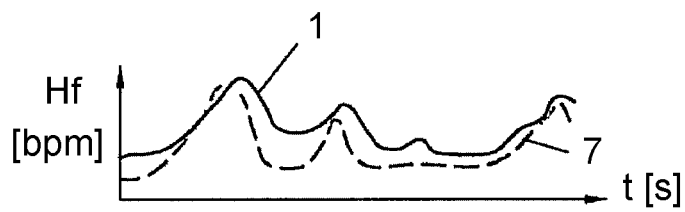
Fig. 3A
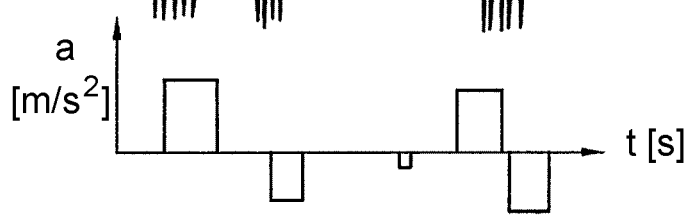
Fig. 3B
Fig. 3C
Fig. 4A
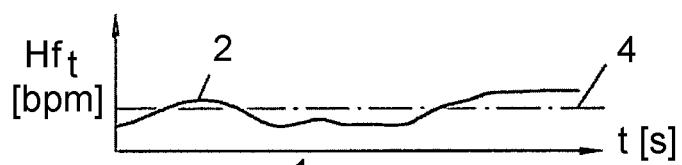
Fig. 4B
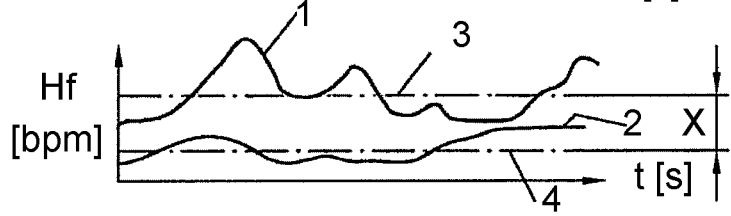
Fig. 4C

METHOD FOR MODIFYING A DRIVING SIMULATOR

CROSS-REFERENCE TO RELATED APPLICATIONS

This application is a U.S. national stage of PCT/EP2014/071633, filed 9 Oct. 2014, which was based on Austrian Application No. A50755/2013, filed 13 Nov. 2013. All priorities are claimed and the prior disclosures are incorporated by reference in their entireties.

BACKGROUND OF THE INVENTION

The present invention relates to a method for modifying a driving simulator.

In recent years, as a result of increasingly radical testing restrictions, especially in racing, it has become common to carry out large portions of training in driving simulators. These driving simulators are often designed in such a manner that the athlete and or driver sits in a cockpit which is attached to a movable platform, and the driver completes training modules on computer-generated race courses. A driving simulator has great potential specifically for simulating events which arise in practice, but for which is it impossible to train, or for which training involves great expense of time and effort. Driving simulators are therefore a reasonable complement to conventional training at the racetrack or on a race course; and the greatest efficiency is achieved by a mix of different training methods.

Driving simulators allow higher training efficiency by using targeted repetition of certain situations. They allow training under highly varied conditions, such as different weather, course properties, vehicle configurations, etc., without placing wear on the actual vehicle and/or increasing the need for parts which wear down. A variety of scenarios can be simulated and repeated as often as desired. The routine recording the training modules typically allows a corresponding analysis of the training.

In the broadest sense, simulators enable action/reaction training within certain limits, and allow athletes to develop sensitivity without taking risks.

However, this is also a specific disadvantage of conventional driving simulators. In actual driving, or in an actual competition scenario, the athlete driver is exposed to a wide range of dangers which threaten the driver himself as well as the vehicle being used. Therefore, a significant factor for the driver is the elevated stress level at which he must control the vehicle during an actual driving event. Even at elevated stress levels, he must be able to make important decisions in the shortest possible period of time. However, this important aspect, which influences the behavior and the performance of the driver to a decisive degree, is particularly given no precedence within the conventional driving simulators. As a result, the result of training is significantly reduced compared to actual driving.

Of course, the problem posed by the difference between reality and training simulations is not limited only to motor sports. It applies as well to other types of sports, which is why, in the following, the driver is referred to in general as an athlete.

SUMMARY OF THE INVENTION

The problem addressed by the invention is that of upgrading a driving simulator and accordingly enhancing the effect of training.

This problem is addressed according to the invention in that, during at least one time segment of an actual drive, a chronological profile of a biometric state of the athlete is determined, in that at least one chronological profile of a parameter of a vehicle used by the athlete is determined, in that a relationship is determined between the chronological profile of the biometric state of the athlete and the at least one chronological profile of the parameter of the vehicle, said relationship giving the change over time of the biometric state according to the change over time of the parameter, in that, during a first training in the driving simulator, a developing chronological training profile of the biometric state of the athlete is determined, and in that, during a further, second training in the driving simulator, the chronological training profile of the biometric state of the athletes, modified by mental stimulation of the athlete according to the determined relationship, is made to approximate the chronological profile of the biometric state of the athlete in the actual drive.

In this way, the training, and/or the chronological profile of a biometric state of the athlete during the training, can be approximated to the chronological profile of the biometric state which corresponds to the actual drive. The term 'approximate' in this case is used to mean that the difference between the chronological profile of a biometric state during an actual drive and the chronological training profile of the biometric state is reduced. The biometric state of an athlete during the training can be adapted selectively by mental stimulation of the athlete according to the parameter.

In one advantageous embodiment, an average is determined over the chronological profile of the biometric state of the athlete during at least one time segment of a real drive, a training average is determined over the chronological training profile of the biometric state of the athlete during the first training in the driving simulator, and during the second training in the driving simulator the training average is approximated to the average by means of mental stimulation of the athlete.

In this way, it is possible, for example, to compare an average stress level which arises during at least one time segment of an actual drive, with that which arises during training. The average stress level during the training can then be later accordingly approximated to that which is experienced during a real drive. The training effect is therefore much higher.

In a further advantageous embodiment, the mental stimulation of the athlete is auditory and/or visual and/or tactile stimuli. In this way, it is possible to effectively influence the chronological training profile of the biometric state of the athlete with minimal technical complexity.

In a further advantageous embodiment, the mental stimulation of the athlete is accomplished using at least one individualized stimulus sequence. This makes it possible to influence the subconscious of the athlete in a targeted manner, and to accordingly instigate a specific chronological training profile of the biometric state of the athlete.

In addition, it is advantageous that the at least one stimulus sequence which influences the chronological training profile of the biometric state of the athlete is determined by experiments during the training. In this way, it is possible to individually determine different stimulus sequences and their influence on the athlete, and the chronological training profile of the biometric state of said athlete, without any danger for the athlete.

BRIEF DESCRIPTION OF THE DRAWINGS

The present invention is described below in greater detail with reference to FIGS. 1 to 5, which show an advantageous embodiment of the invention by way of example, in a schematic manner which shall not be construed as limiting the invention. In the figures, FIGS. 3A-C show the mental stimulation and the effect thereof on the heart rate, FIGS. 4A-C show the difference between the averages of the heart rate during a real drive and during the drive in the driving simulator, in comparison.

DETAILED DESCRIPTION OF THE INVENTION

The method according to the invention is used, by way of example, for optimizing the training of a race driver, wherein the method—as mentioned above—is of course not limited only to motor sports. Rather, it can also be used for other types of sports. For this reason, in the following the race driver and/or driver is referred to in general as an athlete.

The following refers to an actual drive or to a training drive. It should be noted that this does not necessarily mean an entire drive, an entire race time, or completing an entire race course/race track. This context can also include course segments and/or time segments which allow corresponding comparisons.

All data and or values which are determined, measured, or made available, pertaining to the vehicle, the driving simulator, the athlete, and/or his mental stimulation can be processed by a measuring- and/or evaluating- and/or control- and/or calculating unit. However, this is not bound to a particular location. As a result, the captured data can, but need not necessarily, be processed in the vehicle, in the driving simulator, or on the person of the athlete.

Typically, a real drive produces a significantly higher stress level than a drive in the driving simulator, at least in segments or periods of time during the drive. This is easy to comprehend and not particularly remarkable, because in the driving simulator the potential risks to the person and the vehicle are reduced to zero. However, as a result, during the training the reactions off the athlete and/or the ability of the athlete to react are different than during the actual drive.

The stress level can be determined using a variety of biometric data. This includes, by way of example, heart rate, pulse, heart variability, and electrodermal activity—that is, skin conductance—used to measure the stress level, although stress can of course be determined using a variety of other biometric data.

Figure 1A:
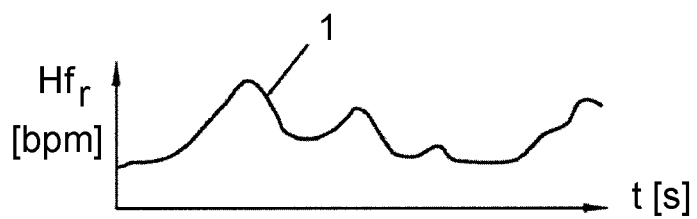
FIGS. 1A-C show the chronological profile of the heart rate according to acceleration and/or speed.
Figure 1B:
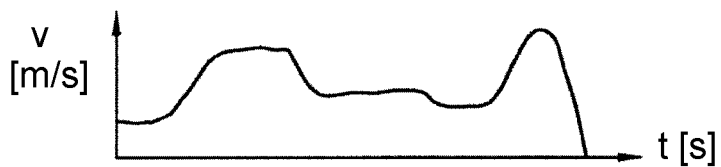
Figure 1C:
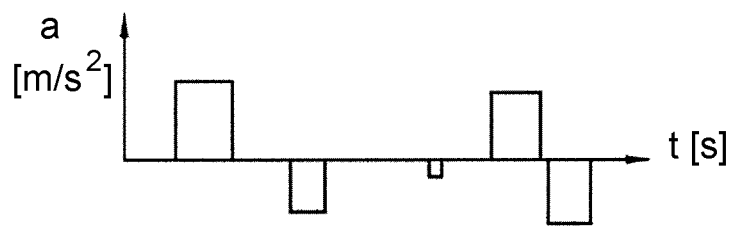

FIG. 1A shows, by way of example, the chronological profile 1 of the heartrate $Hf_r$ according to time, produced along the chronological profile of a longitudinal acceleration a (FIG. 10) and/or the speed v (FIG. 1B) for a time segment of an actual drive. Of course, the term 'longitudinal acceleration a' also means negative acceleration in the longitudinal direction that is, longitudinal deceleration. It can be seen that, by way of example, during and/or after rapid acceleration or deceleration phases which represent changes in the longitudinal acceleration a, the heart rate $Hf_r$ rises accordingly. A very similar chronological profile 1 can of course be produced during transverse acceleration or other forces which are active on the driver.

Such a chronological profile 1 of a biometric state of an athlete is determined and/or recorded in a first step during a time segment, or during an entire, actual drive, for example during an actual training drive or an auto race. In the process, the corresponding biometric state can be determined by means of corresponding sensors. By way of example, if the heart rate Hf is selected as the biometric state, a chest strap such as is known in many uses in both sports and medicine can be used as the measuring device.

The heart rate Hf of the athlete is only named as a biometric state by way of example. As noted above, a variety of other biometric data is also suitable for use as the biometric state. When appropriate sensors and/or measuring units are used, this other biometric data can also be recorded at the same time. In this way, it is also possible to use a plurality of biometric data as the biometric state.

During the actual drive, in addition to the biometric state of the athlete, at least one parameter is determined for a vehicle used by the athlete. In this case, in addition to the heart rate $Hf_r$, chosen by way of example, the same selected hereby way of example as the biometric state of the athlete, the longitudinal acceleration a of the vehicle is determined as the parameter. As noted above, other forces which act on the driver can be used as the parameter.

As can be seen, there is a relationship between the heart rate Hf as the biometric state of the athlete, and, by way of example, the longitudinal acceleration a of the vehicle, as the parameter which is dependent on the driving situation. The relationship reveals the change over time of the biometric state according to the change over time of the parameter, and is determined during at least one time segment of the actual drive.

Figure 2A:
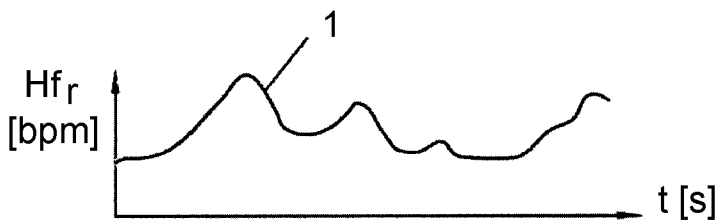
FIGS. 2A-C show the chronological profile of the heart rate during an actual drive, and during the drive in the driving simulator, in comparison.
Figure 2B:
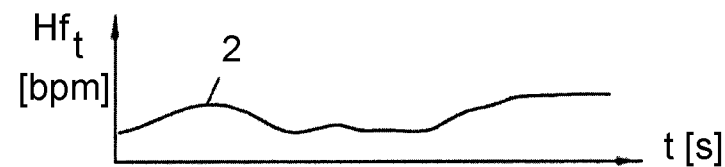
Figure 2C:
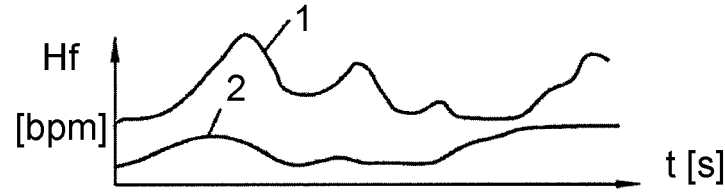

FIG. 2C shows the comparison between the chronological profile 1—illustrated in FIG. 1A/2A—of the heart rate $Hf_r$ and/or the biometric state as can arise during an actual drive, and a chronological training profile 2 of the biometric state (FIG. 2B) as can arise for the same course during a first training in a driving simulator. This resulting chronological training profile 2 of the biometric state of the athlete is recorded and/or determined during the first training in the driving simulator. The training is the process of the athlete completing the same route in the driving simulator, under the same conditions, as the original, actual drive. It must be noted that no precise statements can be made in advance about the chronological profile 1 or about the chronological training profile 2, because they depend on the physiological and psychological state of the athlete.

It can be seen that the chronological profile 1 and the chronological training profile 2 are similar. The chronological training profile 2 from the drive in the driving simulator, however, is attenuated in comparison to the chronological profile 1 from the actual drive.

The heart rate $Hf_t$ achieved during the training does not reach suck high values as during the actual drive. In addition, the rise and fall of the heart rate (heart variability) is less pronounced during the training than during the actual drive. The reason for this is the aforementioned lower risk potential and the resulting lower stress level during the drive in the driving simulator.

In a further step, the athlete completes a second training in the driving simulator in which the course is simulated with the same conditions as the original, actual drive and the first training. As can be seen in FIG. 3B, however, during this second training, the athlete is mentally stimulated by sounds, for example by a sequence of tones played through headphones, and this constitutes auditory stimulation 6. The mental stimulation is performed in phases according to the determined relationship between the biometric state of the athlete and the parameter, preferably specifically in the route segments and/or phases in which the difference between the chronological profile 1 of the biometric state and the chronological training profile 2 is particularly large.

During the second training in the driving simulator, the chronological training profile 7 of the biometric state of the athlete, modified by mental stimulation of the athlete according to the determined relationship, is approximated to the chronological profile 1 of the biometric state of the athlete from the actual drive (see FIG. 3A).

The term 'approximate' in this case is used to mean that the difference between the chronological profile 1 of a biometric state during an actual drive and the chronological training profile 2 of the biometric state is reduced.

The mental stimulation in the form of auditory stimuli 6 is used here only by way of example. The athlete can certainly be mentally stimulated by visual, tactile, or similar stimuli, or by a combination of the same. The mental stimulation is used to actively influence brain activity, thereby changing the biometric state of the driver with the goal of increasing the stress level.

The stimuli 6—which are, by way of example, auditory—are used in a targeted manner, in this case to match the timing of the simulated longitudinal accelerations a (see FIG. 3C). In this way, the heart rate $Hf_t$, by way of example, is matched, according to the longitudinal acceleration a, during the training in the driving simulator to the heart rate which arises during the actual drive.

As can be seen (FIG. 3A), the modified chronological training profile 7 of the biometric state of the athlete corresponds to an approximation (at least in segments) of the chronological profile 1 of the biometric state of the athlete during the real drive. It should be noted that the modification occurs without a change to the simulation itself. The simulated course conditions, such as course width or surface properties, weather, and accordingly visibility conditions, by way of example, remain unchanged and equivalent to the actual drive. Of course, biometric states other than heart rate Hf, and other parameters which are dependent on the driving situation, and the combinations thereof, are also possible.

As also illustrated in FIGS. 3A-C, it is not necessary to use the auditory stimuli 6 over the entire length of the course in order to perform the modification of the driving simulator as described above. The mental stimulation can also be used in only certain stretches of the course, or during certain time segments. By way of example, a modification for very pronounced values of the parameters could be contemplated. For this purpose, the mental stimulation of the athlete would only be used during the training in the driving simulator when, for example, there are very high longitudinal accelerations a and/or other forces.

The mental stimulation of the athlete in this case can be performed using an individualized stimuli sequence. The term 'individualized' is used because, as mentioned above, both the chronological profile 1 and the chronological training profile 2 are dependent on the physiological and psychological state of the athlete. The exact way in which the stimuli sequence which influences the chronological training profile 2 of the biometric state of the athlete, and accordingly produces the modified chronological training profile 7, is characterized is therefore advantageously determined by experiments during the training. At least one individualized stimuli sequence can be assigned to each athlete by these experiments. This makes it possible, by way of example for a certain stretch of the course, to modify the chronological training profile 2 of the biometric state of the athlete and approximate the same to the chronological profile 1 of the biometric state of the athlete. The experiment may reveal, for example, that for another stretch of the course, an entirely other stimuli sequence is necessary to achieve the aforementioned approximation of the two profiles.

It should be noted that the chronological profile 1 of the biometric state of the athlete as determined and/or recorded during a time segment or during an entire, actual drive, can also be used for medical purposes. By way of example, if an accident or the like occurs during the actual drive and results in negative health consequences for the athlete, the data relating to the biometric state can be given to, for example, first responders or other medical personnel. This can enable a more precise preliminary diagnosis and/or more targeted care. In addition, combination with a specific change over time of a parameter helps to reach a medical diagnosis because, when, for example, a longitudinal acceleration a is applied to the athlete during an accident, in this case it is an important clue to the possible severity of the injury.

As noted above, the data and/or values which are measured or presented, pertaining to the vehicle and/or the athlete and/or his mental stimulation are processed by a measuring—and/or evaluation—and/or control—and/or calculating unit which is not fixed at the location. If, by way of example, an evaluating unit is arranged beyond the vehicle, the measured data makes it possible to prevent accidents by, for example detecting an unusual chronological profile 1 early-on during an actual drive, and halting the athlete to end the actual drive.

In a further variant illustrated in FIG. 4A, the average value for the chronological profile 1 of the biometric state of the athlete is calculated during at least one time segment of an actual drive, in the form of an average 3. The average 3 can be calculated over a certain stretch of the route, or over the entire drive. As for the chronological profile 1, an average is calculated in the form of a training average 4 for the chronological training profile 2 of the biometric state of the athlete during a first training as well (FIG. 4B).

As can be seen in FIG. 4C, the training average 4 differs from the average 3 by the difference X. On average, the driver is "less stressed" during the training by this difference X. As noted above, the behavior and the performance of the athlete during training differs from those in an actual drive or a race/competition because of this difference X.

As described above for FIGS. 3A-C, the athlete completes a second training in the driving simulator in which the course is simulated with the same conditions as the original, actual drive and the first training.

Figure 5A:
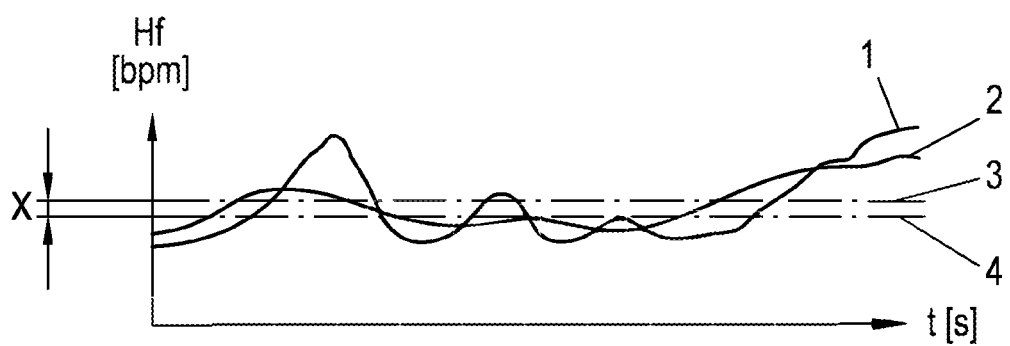
FIGS. 5A-B show the approximation of the average as the result of mental stimulation.
Figure 5B:
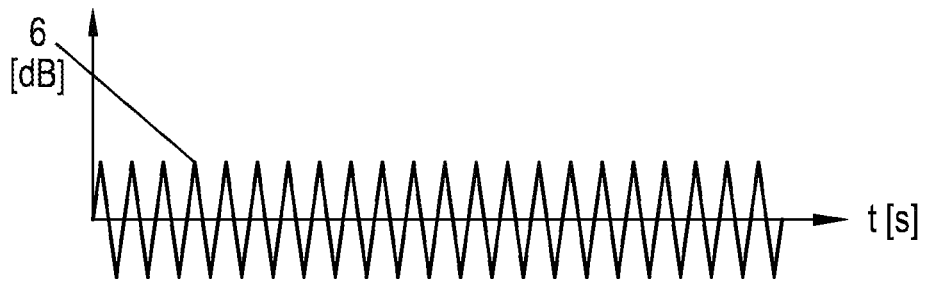

As shown in FIGS. 5A-B, the athlete is again mentally stimulated during this second training. In this way, during the second training in the driving simulator, the training average 4 is approximated to the average 3 by the mental stimulation of the athlete (FIG. 5A). In this variant, however, the auditory stimulus 6 is not given according to the parameter, but rather, by way of example, constantly over the entire training drive and/or over the corresponding stretch or time segment (FIG. 5B). However, the auditory stimulus 6 need not be given during the entire training drive or the corresponding stretch or time segment.

As a result of this mental stimulation, the biometric state and/or the training average 4 thereof is/are modified, and thereby made to approximate the average 3 of the biometric state during the actual drive. In this process, the difference X between the average 3 and the training average 4 is reduced. It should once more be noted that this occurs without changing the simulation itself, and the simulated course conditions remain unchanged and equivalent to the actual drive.

The approximation of the training average 4 to the average 3, and/or the reduction of the difference X, can occur iteratively over the course of multiple training drives, wherein, as mentioned above, the simulation of the actual drive is not changed. During each training drive, the chronological training profile 2 of the heart rate Hf$_f$, and/or the training average 4 thereof, is determined as the biometric state, the same having changed as a result of the mental stimulation. This process can be carried out as long and/or often as necessary for the training average 4 of the biometric state to approximate, due to the mental stimulation of the athlete, the average 3 of the biometric state. The determination is thereby made as to how the, by way of example, auditory stimuli 6 must be given to cancel out the difference X between the average 3 and the training average 4 of the biometric state, and/or between the actual drive and the training in the driving simulator. By way of example, a corresponding frequency is determined, by means of which the auditory stimuli 6 must be produced such that a given difference X between the average 3 and the training average 4 can be cancelled out.

As mentioned above, this mental stimulation in this second variant is not performed variably over time. The athlete is accordingly mentally stimulated over the entire drive in the driving simulator such that the training average 4—that is, the average stress level during the drive in the driving simulator—approximately corresponds to the average 3 that is, the average stress level during the actual drive.

Over the course of subsequent training drives in the driving simulator, the, by way of example, auditory stimuli determined in this manner are used to accordingly modify the driving simulator.

The precise manner in which the mental stimulation is carried out depends both on the athlete himself and on the manner of the mental stimulation. In the mental stimulation using auditory stimuli 6 as an example, the frequency of a tone sequence may be decisive, for example. How, or how intensively, a driver is mentally stimulated, and/or how strong the effects are relative to the second biometric state, can depend on the aforementioned manner in which the mental stimulation is carried out.

Consequently, the iterative determination explained above helps to optimally adapt the method to different drivers.

The invention claimed is:

1. A method for modifying a driving simulator, comprising:
   providing a driving simulator;
   detecting, by at least one sensor, a biometric state of an athlete driving a vehicle during an actual drive;
   storing the biometric state on at least one non-transitory computer readable media;
   detecting, by the at least one sensor, a vehicle parameter of the vehicle during the actual drive;
   storing the vehicle parameter on the at least one non-transitory computer readable media;
   determining, with a calculating unit, a relationship between the biometric state and the vehicle parameter, the relationship including a change over time of the biometric state according to a change over time of the vehicle parameter;
   determining a training profile of the biometric state during a first training in the driving simulator;
   modifying, with a control unit, the training profile during a second training in the driving simulator, the modifying including stimulating the athlete according to the relationship to approximate the biometric state during the actual drive.

2. The method according to claim 1, wherein an average is determined over a chronological profile of the biometric state of the athlete during at least one time segment of the actual drive, in that a training average is determined over the training profile of the biometric state during the first training in the driving simulator, and in that during the second training in the driving simulator, the training average is made to approximate the average by mental stimulation of the athlete.

3. The method according to claim 1, wherein the stimulating the athlete comprises auditory stimuli.

4. The method according to claim 3, wherein the stimulating the athlete is accomplished using at least one individualized stimulus sequence.

5. The method according to claim 4, wherein the at least one individualized stimulus sequence is determined by experiments during development of the training profile.

6. The method according to claim 1, wherein the stimulating the athlete comprises visual stimuli.

7. The method according to claim 1, wherein the stimulating the athlete comprises tactile stimuli.

8. A driving simulator performing the method of claim 1.

9. A driving simulator system, comprising:
   a driving simulator;
   a biometric state of an athlete driving a vehicle during an actual drive detected by a least one sensor, the biometric state stored on at least one non-transitory computer readable media;
   a vehicle parameter of the vehicle during the actual drive detected by the at least one sensor, the vehicle parameter stored on the at least one non-transitory computer readable media;
   a calculating unit determining a relationship between the biometric state and the vehicle parameter, the relationship including a change over time of the biometric state according to a change over time of the vehicle parameter;
   a training profile of the biometric state determined during a first training in the driving simulator;
   a control unit modifying the training profile during a second training in the driving simulator, the modifying including stimulating the athlete according to the relationship to approximate the biometric state during the actual drive.

10. The system of claim 9, wherein the biometric state and the vehicle parameter each comprise a chronological profile of the actual drive.

11. The system of claim 9, wherein the second training comprises a training module for a computer-generated race course completed by the athlete on the driving simulator.

12. The system of claim 9, wherein the modifying the training profile during the second training comprises comparing a first average stress level during a time segment of the actual drive with a second average stress level during the time segment of the second training.

13. The system of claim 9, wherein the modifying the training profile during the second training occurs without a change to a simulation.

14. The system of claim 13, wherein course conditions in the simulation remain equivalent to the actual drive.

15. The system of claim 9, wherein the stimulating the athlete comprises using a tone sequence.

\* \* \* \* \*